(12) United States Patent
Goldberg

(10) Patent No.: US 9,878,175 B2
(45) Date of Patent: Jan. 30, 2018

(54) PAIN RELIEVING FABRIC

(71) Applicant: Silvon, LLC, Englewood Cliffs, NJ (US)

(72) Inventor: Arthur Goldberg, Livingston, NJ (US)

(73) Assignee: Silvon, LLC, Englewood Cliffs, NJ (US)

(*) Notice: Subject to any disclaimer, the term of this patent is extended or adjusted under 35 U.S.C. 154(b) by 197 days.

(21) Appl. No.: 14/948,815

(22) Filed: Nov. 23, 2015

(65) Prior Publication Data

US 2017/0246469 A1    Aug. 31, 2017

(51) Int. Cl.
*A61N 1/00* (2006.01)
*A61N 2/00* (2006.01)
*A61N 2/02* (2006.01)

(52) U.S. Cl.
CPC .............. *A61N 2/008* (2013.01); *A61N 2/02* (2013.01)

(58) Field of Classification Search
CPC ............. A61N 2/00; A61N 2/008; A61N 2/02
USPC ........................................................ 600/9–15
See application file for complete search history.

(56) References Cited

U.S. PATENT DOCUMENTS

| 6,860,122 B2 | 3/2005 | Goldberg |
| 2003/0186608 A1 | 10/2003 | Goldberg |
| 2008/0119773 A1 | 5/2008 | Flick |

FOREIGN PATENT DOCUMENTS

EP    2208817 A1    7/2010

*Primary Examiner* — John Lacyk
(74) *Attorney, Agent, or Firm* — Richard M. Goldberg

(57) ABSTRACT

A fabric for producing an induced electromagnetic field in the presence of a human body to reduce endogenous pain, includes a non-conductive base fabric, a plurality of parallel, spaced apart electrically conducting carbon fibers interspersed in the base fabric constituting approximately 3% of the weight of the fabric, and a plurality of parallel, spaced apart electrically conducting silver fibers interspersed in the base fabric constituting approximately 6% of the weight of the fabric, and being in parallel, spaced apart relation to the electrically conducting carbon fibers.

19 Claims, 2 Drawing Sheets

PAIN RELIEVING FABRIC

BACKGROUND OF THE INVENTION

The present invention relates generally to fabrics and articles of clothing made from fabrics, and more particularly, is directed to fabrics and articles of clothing made from these fabrics that have a beneficial pain relieving effect.

It is known that electrically conductive fibers in a fabric are intended to create an electromagnetic (EM) field or EMF from the electrical signals transmitted throughout a person's body, thereby reducing the feeling of pain and discomfort.

U.S. Pat. No. 6,860,122 to the same inventor herein discloses a fabric for reducing endogenous pain by application of the fabric to a pain site to facilitate the flow of endogenous electrical current in the body. The fabric includes a knitted stretch fabric having a knit base structure of electrically non-conductive fibers forming courses and wales, a first electrically-conductive carbon fiber knitted into and extending along first selected wales and transversely along first selected courses of the base structure, and a second electrically-conductive carbon fiber knitted into and extending along second selected wales and transversely along second selected courses of the base structure intersecting the first selected courses for contacting the first electrically-conductive carbon fiber and thereby defining a matrix of first and second electrically-conductive carbon fibers that induce an electrical current in the presence of an electrical charge.

However, it has been found that the formation of the two electrically-conductive carbon fibers in a matrix such that the first electrically-conductive carbon fibers contact the second electrically-conductive carbon fibers, inhibits the induced electrical current, thereby reducing the beneficial pain-relieving effect.

Further, because carbon fibers are not highly electrically conductive, the voltage generated in these fibers is not very high, that is, the created EM field is small. Even though carbon fibers are not highly electrically conductive, and therefore not very efficient in creating an EM field, a large reason for using these carbon fibers is because of their low cost as compared to highly conductive metal materials.

It is also known to add silver fibers to fabrics because of the moisture wicking and antibacterial properties of the silver. Silver is also known for its conductivity characteristics in clothing.

Generally, when silver is added to a fabric, it functions as to high level grounding, static discharge, electric field shielding, and radiofrequency (RF) shielding, particularly in anti-static environments. Because it has been used for its shielding effects, silver would never be used in an environment in order to generate EM fields for healing purposes, let alone in combination with carbon.

A problem, however, is that silver is a relatively expensive fiber, so that manufacturing a fabric with a large percentage of silver fibers becomes cost prohibitive.

Further, it has not been known to combine carbon fibers with silver fibers in the same fabric, in view of their very different effects and desired results.

SUMMARY OF THE INVENTION

Accordingly, it is an object of the present invention to provide fabrics and articles of clothing made from these fabrics that overcome the aforementioned problems.

It is another object of the present invention to provide fabrics and articles of clothing made from these fabrics that have a beneficial pain relieving effect.

It is still another object of the present invention to provide fabrics and articles of clothing made from these fabrics that provide a combination of electrically conductive carbon fibers with electrically conductive silver fibers.

It is still another object of the present invention to provide fabrics and articles of clothing made from these fabrics in which the carbon fibers and silver fibers run in parallel, spaced relation.

It is still another object of the present invention to provide fabrics and articles of clothing made from these fabrics in the carbon fibers and silver fibers produce a synergistic EMF effect, that functions to reduce pain.

In accordance with an aspect of the present invention, a fabric for producing an induced electromagnetic field, includes a non-conductive base fabric, a plurality of parallel, spaced apart electrically conducting carbon fibers interspersed in the base fabric, and a plurality of parallel, spaced apart electrically conducting silver fibers interspersed in the base fabric in parallel, spaced apart relation to the electrically conducting carbon fibers.

Preferably, the ratio of silver fibers to carbon fibers is in a weight range of 1:1 to 3:1, and more preferably, is approximately 2:1.

Preferably, the carbon fibers range from approximately 3% to 8% of the weight of the fabric and the silver fibers range from approximately 3% to 10% of the weight of the fabric, and more preferably, the silver fibers comprise approximately 6% of the weight of the fabric.

In accordance with another aspect of the present invention, a method of reducing endogenous pain by creating an induced electromagnetic field in the presence of a human body, includes the steps of knitting a fabric comprised of a non-conductive base fabric, a plurality of parallel, spaced apart electrically conducting carbon fibers interspersed in the base fabric, and a plurality of parallel, spaced apart electrically conducting silver fibers interspersed in the base fabric in parallel, spaced apart relation to the electrically conducting carbon fibers; applying the fabric close to a pain site; and maintaining the fabric close to the pain site for the duration of desired relief.

The fabric can be formed into a structure selected from the group consisting of garments, bandages and supporting structures. Specifically, the garments are selected from the group consisting of gloves, head bands, knee bands, wrist bands, elbow bands, ankle bands, outer garments and undergarments, large body bands, facial masks, caps, hats and shoe inserts; while the supporting structures are selected from the group consisting of seat cushions, pet cushions, bedding sheets, pillowcases and mattress covers.

In accordance with another aspect of the present invention, an article of manufacture includes a fabric for producing an induced electromagnetic field, the fabric comprising a non-conductive base fabric, a plurality of parallel, spaced apart electrically conducting carbon fibers interspersed in the base fabric, and a plurality of parallel, spaced apart electrically conducting silver fibers interspersed in the base fabric in parallel, spaced apart relation to the electrically conducting carbon fibers.

The above and other features of the invention will become readily apparent from the following detailed description thereof which is to be read in connection with the accompanying drawings.

DETAILED DESCRIPTION

Figure 1:
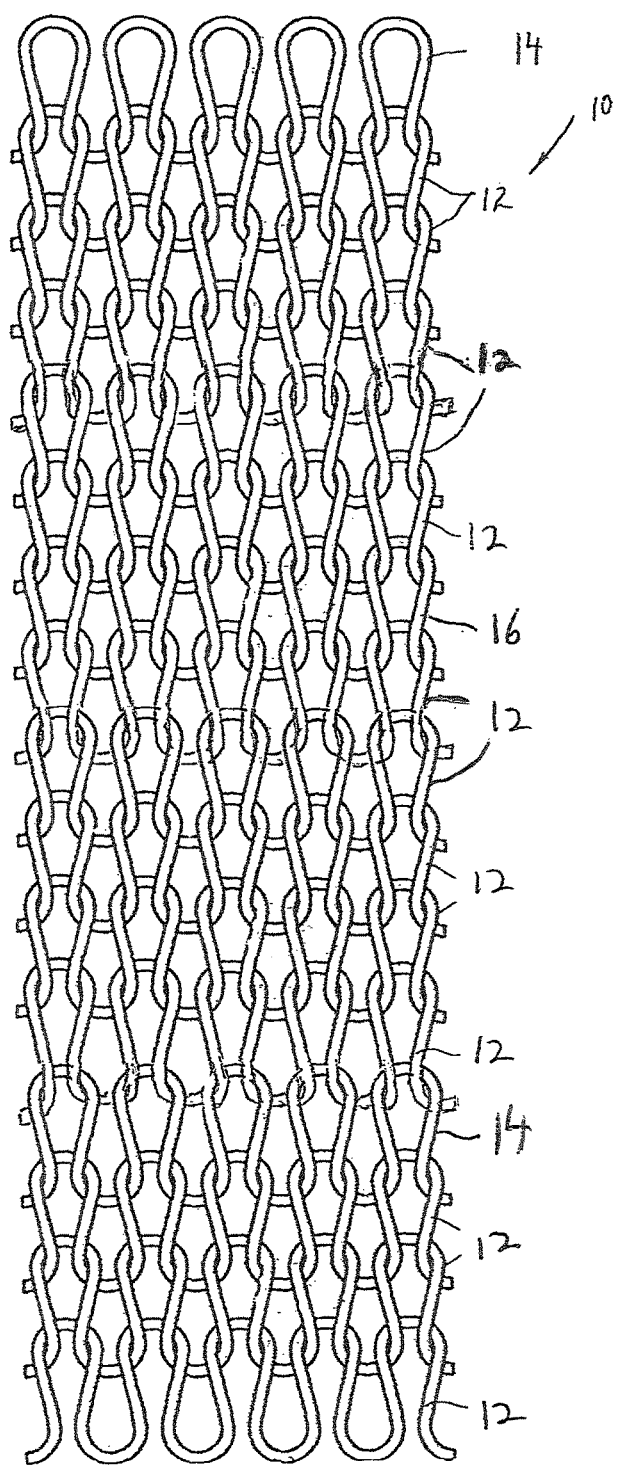
FIG. 1 is a top plan view of a first weft fabric structure according to the present invention.

Referring to the drawings in detail, and initially to FIG. 1, a knit fabric 10 according to the present invention is formed in a conventional manner with polyester weft fibers 12 extending horizontally of the fabric and looped together. There are no warp fibers. Knit fabric 10 can be formed on any suitable circular knitting machine, for forming a single knit fabric as shown in FIG. 1, or a double knit fabric (not shown). For example, a circular knitting machine sold by Monarch Knitting Machine Co. of Japan can be used, having a 30 inch diameter, 28 cut (needles per inch), with 48 fiber feeds. It will be appreciated that any other suitable machines can be used, for example, other diameter double knit or single knit machines including proportional needles per inch, using 24, 48 or 60 fiber feeds.

Figure 2:
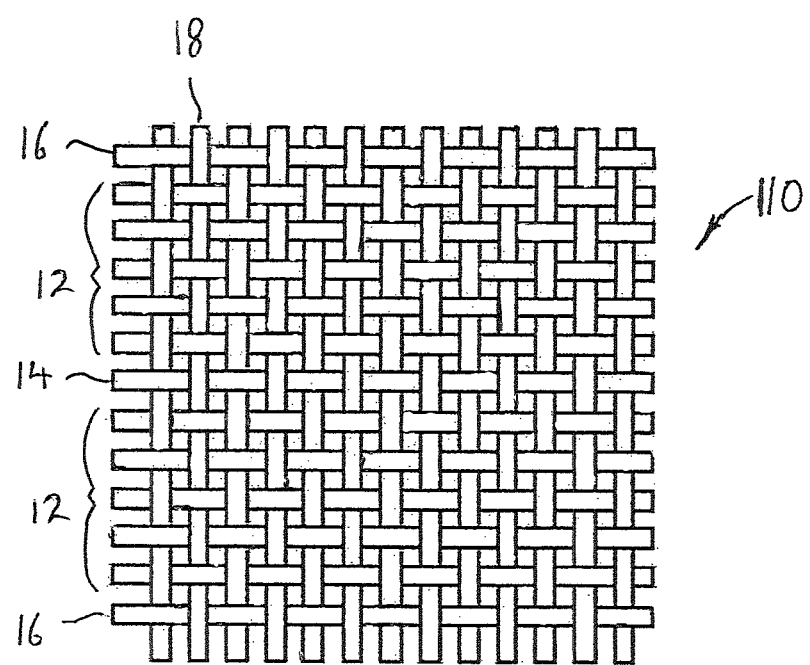
FIG. 2 is a top plan view of a second woven fabric structure according to the present invention.

However, the present invention can be used with any type of knitting operation, such as a warp knitting machine, a weaving machine, etc. Thus, for example, as shown in FIG. 2, for a woven fabric 110, two threads 16 of silver are run together in a feed, followed by 5 threads 12 of polyester, followed by one thread 14 of carbon, followed by 5 threads 12 of polyester, and this pattern repeating throughout the fabric. The cross woven fibers 18 are polyester.

Based on the machine diameter, proportional open flat widths can be made. The weight range of the fabric can vary from about 4.0 oz/square yard to about 16.0 oz/square yard, based on denier (fiber sizes) used, and is preferably 8.0-8.8 oz/square yard, finished at 66 inch open flat width.

In accordance with the present invention, it has been found that the combination of electrically conductive carbon fibers with silver fibers in a parallel, spaced apart, non-contacting arrangement, provides a synergistic effect that creates an optimum EM field for reducing pain and increasing healing in a person wearing the fabric.

In this regard, electrically-conductive carbon fibers 14 replace some of the weft fibers 12, while conductive silver fibers 16 replace others of the weft fibers 12, with the electrically-conductive carbon fibers 14 and conductive silver fibers 16 being arranged in a parallel, spaced apart, non-contacting arrangement. Preferably, the percentage of electrically-conductive carbon fibers 14 is about 3% by weight of the total fibers in the fabric, while the percentage of conductive silver fibers 16 is about 6% by weight of the total fibers in the fabric, although the present invention is not limited thereto.

In forming this fabric, as shown in FIG. 1, two threads 16 of silver are run together in a feed, followed by 5 threads 12 of polyester, followed by one thread 14 of carbon, followed by 5 threads 12 of polyester, and this pattern repeating throughout the fabric.

EXAMPLE 1

For example, the denier sizes and percentages of fibers used can be as follows for a double knit fabric:

First layer or ply of fabric:

Feeds 1-48: 1/70/36 textured polyester comprising 100% by weight of the fabric, where 70 is the denier and 36 represents the number of filaments in the denier, sold by Unifi, Inc. of Greensboro, N.C., for the back layer of fabric.

Second layer or ply of fabric:

Feeds 1, 15, 27, 39: 1/25/3 carbon composite comprising 3% by weight of the fabric, namely, a fine-filament bi-component fiber made with a trilobal conducting carbon sold under the trademark NEGA-STAT Model P210 by William Barnet & Son, LLC of Spartanburg, S.C., where 1 represents the single thread, 25 is the denier and 3 represents the number of filaments in the yarn, Feeds 9 and 33: 1/70/34 silver composite comprising 6% by weight of the fabric, sold under the trademark X-STATIC by Noble Biomaterials, Inc. of Scranton, Pa., where 1 represents the single thread, 70 is the denier and 34 represents the number of filaments in the yarn, Feeds 2-8, 10-14, 16-26, 28-32, 34-38, 40-48: 1/70/36 textured polyester comprising 91% by weight of the fabric, where 1 represents the single thread, 70 is the denier, 36 represents the number of filaments in the yarn, sold by Unifi, Inc. of Greensboro, N.C.

In forming this fabric, as shown in FIG. 1, two threads of silver were run together in a feed, followed by 5 threads of polyester, followed by one thread of carbon P210, followed by 5 threads of polyester, and this pattern repeating throughout the fabric.

With the above arrangement, either the first or second layer can be positioned in contact with the skin of a person, since the beneficial effect is achieved by the induced EM field.

However, the second layer has the silver and carbon exposed on a first side and only the polyester exposed on the second side. In areas where there would be perspiration, it is advisable that the second side be in contact with the skin of the person, since the perspiration may short out some of the effects of the silver. However, in order situations where there would be little or no perspiration, the silver and carbon side can be in contact with the skin of the person.

EXAMPLE 2

In this example, the first layer is replaced by a layer that is identical with the second layer having the silver and carbon fibers. In such case, the polyester exposed second side of one layer would be in contact with the silver and carbon exposed first side of the other layer.

It will be appreciated that the above is only one example. Other fabric embodiments may include denier size ranges, for example, from 30 to 100 denier sizes of the silver fibers sold under the trademark X-STATIC, 25 to 70 denier sizes of the carbon fibers sold under the trademark NEGA-STAT, and 40 to 150 textured or non-textured polyesters.

Further, although a fast-acting and more conductive carbon fiber sold under the trademark NEGA-STAT Model P210 by William Barnet & Son, LLC of Spartanburg, S.C. was used, a slower-acting and less conductive carbon fiber sold under the trademark NEGA-STAT Model P190 (1/70/12) by William Barnet & Son, LLC of Spartanburg, S.C. can be used as well.

With the above arrangement, various tests were performed, as follows, on various fabrics, in order to detect voltages, and therefore, EM fields generated.

Specifically, various fabrics were tested.

In a first test on a small patch of fabric of an area of 8" by 10" with a polyester base, the following results were achieved:

TABLE 1

| Type of Fabric | Ambient Light | Close CFL (23 watts) |
| --- | --- | --- |
| Dual Twisted Carbon Alone | 100 mV | 125 mV |
| Silver Alone | 110 mV | 170 mV |
| Silver/Carbon | 100 mV | 200 mV |

The first column shows the type of fabric used in the test, namely, two carbon fibers in contact with each other, to simulate an effect similar to that of U.S. Pat. No. 6,860,122; silver fibers alone in the fabric; and lastly, silver fibers and carbon fibers in a parallel, spaced apart, non-contacting arrangement according to the present invention. The laboratory conditions were 73° F. with a relative humidity of 12%.

The dual twisted carbon fabric contained a series of two carbon fibers twisted together, one carbon fiber being the fast-acting conductive carbon fiber 1/25/3 sold under the trademark NEGA-STAT Model P210 by William Barnet & Son, LLC of Spartanburg, S.C. and comprising 3% of the weight of the fabric, and the other carbon fiber being the slower-acting conductive carbon fiber 1/70/12 sold under the trademark NEGA-STAT Model P190 by William Barnet & Son, LLC of Spartanburg, S.C. and comprising 8.5% of the weight of the fabric, with the remainder of the fabric being polyester comprising 88.5% of the weight of the fabric. In forming this fabric, there were 1 two twisted carbon fibers P190 and P210, followed by 11 polyester fibers, and this pattern repeating throughout the fabric. The voltage was measured on a single line of twisted carbon threads.

The silver fibers alone in the fabric were formed by 1/70/34 silver composite comprising 6% by weight of the fabric, with the remainder of the fabric being polyester comprising 94% of the weight of the fabric. In forming this fabric, two threads of silver were run together in a feed, followed by 11 threads of polyester, and this pattern repeating throughout the fabric. The voltage was measured on a single line of silver threads.

Lastly, the silver/carbon fabric was formed in the manner of the second layer of fabric discussed above in Example 1, according to the present invention. In forming this fabric, two threads of silver were run together in a feed, followed by 5 threads of polyester, followed by one thread of carbon P210, followed by 5 threads of polyester, and this pattern repeating throughout the fabric. The voltage was measured on a single line of silver threads.

As shown by Table 1, in the presence of ambient light in the room, each fabric exhibited a similar generated voltage in the fibers of the fabric, which corresponds to an equal electromagnetic field.

When a 23 watt compact fluorescent lamp (CFL) bulb was brought to a position about eight inches from the fabric, the induced voltages increased, with the dual twisted carbon fabric exhibiting the least increase to 125 mV, the silver alone fabric exhibiting the next increase to 170 mV, and the silver/carbon fabric according to the present invention exhibiting the largest increase to 200 mV.

It will be appreciated that the induced voltage, and thereby the induced EM field, in this example was created by a 23 watt compact fluorescent lamp (CFL) bulb. In use, the induced voltage, and thereby the induced EM field, would be created by anything nearby that would produce such voltage, including a human body.

In a second test on a larger patch of fabric of an area of 8" by 36" with a polyester base, the following results were achieved, measured on one line:

TABLE 2

| Type of Fabric | Ambient Light | Close CFL (23 watt) |
| --- | --- | --- |
| Silver Alone | 900 mV | 1000 mV |
| Silver/Carbon | 1000 mV | 1250 mV |

The fabrics were formed in the same manner discussed above as to the smaller samples of Table 1.

The voltage for each fabric was measured on a single line of silver threads.

When a 23 watt compact fluorescent lamp (CFL) bulb was brought to a position about eight inches from the fabric, the induced voltages increased, the silver alone fabric exhibiting the smallest increase to 1000 mV, and the silver/carbon fabric according to the present invention exhibiting the largest increase to 1,250 mV.

In a third test on the larger patches of fabric with a polyester base, the following results were achieved, where the voltage for each fabric was measured on three lines of silver threads.

TABLE 3

| Type of Fabric | Ambient Light | Close CFL |
| --- | --- | --- |
| Silver Alone | 1050 mV | 1250 mV |
| Silver/Carbon | 1750 mV | 2000 mV |

When a 23 watt compact fluorescent lamp (CFL) bulb was brought to a position about eight inches from the fabric, the induced voltages increased, the silver alone fabric exhibiting the smallest increase to 1250 mV, and the silver/carbon fabric according to the present invention exhibiting the largest increase to 2000 mV.

It is therefore seen that the combination of the carbon fibers and silver fibers according to the present invention in a parallel, spaced apart, non-contacting arrangement, provided a synergistic effect, greater than the silver alone or twisted carbon alone. This created a larger voltage flow through the fabric, with a consequent larger induced electromagnetic field, to create a greater pain reducing effect and greater healing effect. In effect, the silver picked up or enhanced the EM field from the carbon fibers.

The fabric of the present invention is adapted to various products to produce these beneficial effects, including, but not limited to, garments, bandages and supporting structures. For example, the garments can include gloves, head bands, knee bands, wrist bands, elbow bands, ankle bands, outer garments and undergarments, large body bands such as back bands, facial masks, caps, hats and shoe inserts. The supporting structures can include, for example, seat cushions, pet cushions, bedding sheets, pillowcases and mattress covers. Because induced EM fields are created, the present invention is effective either directly on the skin of a person or through layers of clothing.

The present invention can also be used to produce fabric using small diameter circular machines usually used for producing hosiery. Tubular sleeves of fabric can be formed and sewn into bands for application to smaller body parts such as a person's arm, elbow, ankle and foot. These preferred embodiments can be manufactured on a machine, for example, made by Lonati SpA of Italy with a four inch diameter and 75 cut (needles per inch), although other similar machines are globally available.

Since antenna attenuation is directly related to antenna area, these smaller products are produced with a higher percentage of silver composite and carbon composite yarns to enable similar area voltages compared to more open width fabrics. It is recommended to have a minimum of 6% silver composite and 3% carbon composite yarns for the fabric to produce an effective electromagnetic field while also ensuring the desired antimicrobial properties.

EXAMPLE 3

For example, the denier sizes and percentages of fibers for a single ply fabric can be:

Feed 1: 1/70/34 textured nylon of 1/120 Lycra covered with a 1/40 textured nylon from Unifi, Inc. of Greensboro, N.C., Feed 2: 1/25/3 carbon composite sold under the trademark NEGA-STAT Model P210 by William Barnet & Son, LLC of Spartanburg, S.C., plus a 1/40/13 textured stretch nylon, Feed 3: 1/120 Lycra™ elastomeric fiber with a 1/40/13 textured stretch nylon.

Feed 4: 1/30/10 silver composite sold under the trademark X-STATIC by Noble Biomaterials, Inc. of Scranton, Pa., plus a 1/40/13 textured stretch nylon.

With the above, the fiber percentage content is preferably 70 denier textured nylon comprising 77% by weight of the fabric, 120 denier Lycra plus 40 denier textured stretch nylon comprising 10% by weight of the fabric, 30 denier X-STATIC silver composite comprising 10% by weight of the fabric, and 25 denier carbon composite NEGA-STAT P210 comprising 3% of the weight of the fabric.

Other embodiments may include 30 denier to 70 denier silver composite yarns in conjunction with 100 denier to 300 denier Lycra and 20 denier to 100 denier textured nylon on circular knitting machines with various diameters.

From the above, preferably, for best performance, the relative percentage content of silver fiber and carbon fiber, is derived from a 2:1 ratio of silver fibers to carbon fibers by weight, although the percentage ratio can be as small as 1:1 and as high as 3:1 or more.

Preferably, the carbon fibers 14 range from 3% to 8% of the weight of the fabric and the silver fibers 16 range from approximately 3% to 10% of the weight of the fabric.

In addition to the above, the use of the silver fibers will increase the life of the fabric since it promotes antimicrobial properties due to silver ion activity. This can be further enhanced with additional surface application of chemical finish products such as that sold under the mark AEGIS by Microban Products Company of Huntersville, N.C.

It will be appreciated that the fabric of the present invention can be used in other applications. For example, it is known that a triboelectric charge is a type of contact electrification in which certain materials become electrically charged after they come into friction contact with a different material. Such triboelectric charge has been used in clothes dryers in order to soften the clothes during a drying operation. Specifically, it has been known to provide balls of wool or balls containing magnets in a clothes dryer in order to soften the clothes.

In this regard, a dryer sheet formed from the fabric of the present invention, for example, as shown in FIG. 1, can be added to a clothes dryer during a drying operation, and because of the silver threads therein, an enhanced triboelectric charge will be created which functions to soften the clothes in the dryer due to the rubbing or friction action. In effect, the dryer sheet will create an EM field that will soften the clothes. The advantage is that such a sheet can be used over and over, without discarding the same, as normally occurs with conventional dryer sheets, such as those sold under the trademark BOUNCE.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention as defined by the appended claims.

What is claimed is:

1. A fabric for producing an induced electromagnetic field, comprising:
   a non-conductive base fabric having a first layer,
   a plurality of parallel, spaced apart electrically conducting carbon fibers interspersed in said first layer of said base fabric with none of said carbon fibers contacting each other, and
   a plurality of parallel, spaced apart electrically conducting silver fibers interspersed in said first layer of said base fabric with none of said silver fibers contacting each other, and
   said silver fibers being in parallel, spaced apart relation to said electrically conducting carbon fibers in said same first layer of said base fabric, with none of said silver fibers contacting said carbon fibers.

2. A fabric according to claim 1, wherein a weight ratio of silver fibers to carbon fibers is in a range of 1:1 to 3:1.

3. A fabric according to claim 2, wherein a weight ratio of silver fibers to carbon fibers is approximately 2:1.

4. A fabric according to claim 1, wherein the carbon fibers range from 3% to 8% of the weight of the fabric and the silver fibers range from approximately 3% to 10% of the weight of the fabric.

5. A fabric according to claim 4, wherein the silver fibers comprise approximately 6% of the weight of the fabric.

6. A method of making and using a fabric for reducing endogenous pain by creating an induced electromagnetic field in the presence of a human body, comprising the steps of:
   knitting a fabric comprised of:
      a non-conductive base fabric having a first layer,
      a plurality of parallel, spaced apart electrically conducting carbon fibers interspersed in said first layer of said base fabric with none of said carbon fibers contacting each other, and
      a plurality of parallel, spaced apart electrically conducting silver fibers interspersed in said first layer of said base fabric with none of said silver fibers contacting each other, and
      said silver fibers being in parallel, spaced apart relation to said electrically conducting carbon fibers in said same first layer of said base fabric, with none of said silver fibers contacting said carbon fibers;
   applying the fabric close to a pain site; and
   maintaining the fabric close to the pain site for the duration of desired relief.

7. A method according to claim 6, further including the step of fabricating the fabric into a structure selected from the group consisting of garments, bandages and supporting structures.

8. A method according to claim 7,
   wherein the garments are selected from the group consisting of gloves, head bands, knee bands, wrist bands, elbow bands, ankle bands, outer garments and undergarments, large body bands, facial masks, caps, hats and shoe inserts; and wherein the supporting structures are selected from the group consisting of seat cushions, pet cushions, bedding sheets, pillowcases and mattress covers.

9. A method according to claim 6, wherein the step of knitting including the step of knitting the fabric with a weight ratio of silver fibers to carbon fibers in a range of 1:1 to 3:1.

10. A method according to claim 9, wherein the step of knitting including the step of knitting the fabric with a weight ratio of silver fibers to carbon fibers of approximately 2:1.

11. A method according to claim 6, wherein the step of knitting includes the step of knitting the fabric with the carbon fibers range from approximately 3% to 8% of the weight of the fabric and the silver fibers range from approximately 3% to 10% of the weight of the fabric.

12. A fabric according to claim 4, the step of knitting including the step of knitting the fabric with the silver fibers comprising approximately 6% of the weight of the fabric.

13. An article of manufacture including a fabric for producing an induced electromagnetic field, the fabric comprising:
a non-conductive base fabric having a first layer,
a plurality of parallel, spaced apart electrically conducting carbon fibers interspersed in said first layer of said base fabric with none of said carbon fibers contacting each other, and
a plurality of parallel, spaced apart electrically conducting silver fibers interspersed in said first layer of said base fabric with none of said silver fibers contacting each other, and
said silver fibers being in parallel, spaced apart relation to said electrically conducting carbon fibers in said same first layer of said base fabric, with none of said silver fibers contacting said carbon fibers.

14. An article of manufacture according to claim 13, wherein a weight ratio of silver fibers to carbon fibers is in a range of 1:1 to 3:1.

15. An article of manufacture according to claim 14, wherein a weight ratio of silver fibers to carbon fibers is approximately 2:1.

16. An article of manufacture according to claim 13, wherein the carbon fibers range from 3% to 8% of the weight of the fabric and the silver fibers range from approximately 3% to 10% of the weight of the fabric.

17. An article of manufacture according to claim 16, wherein the silver fibers comprise approximately 6% of the weight of the fabric.

18. An article of manufacture according to claim 13, wherein the article of manufacture is a structure selected from the group consisting of garments, bandages and supporting structures.

19. An article of manufacture according to claim 18, wherein the garments are selected from the group consisting of gloves, head bands, knee bands, wrist bands, elbow bands, ankle bands, outer garments and undergarments, large body bands, facial masks, caps, hats and shoe inserts; and
wherein the supporting structures are selected from the group consisting of seat cushions, pet cushions, bedding sheets, pillowcases and mattress covers.

* * * * *